(12) United States Patent
Sabati et al.

(10) Patent No.: US 9,078,683 B2
(45) Date of Patent: Jul. 14, 2015

(54) SYSTEMS AND METHODS FOR A MULTIFUNCTION SURGICAL APPARATUS

(75) Inventors: Tzachi Sabati, Megadim (IL); Yacov Domankevitz, Zichron Yacov (IL); Sahar Vilan, Atlit (IL)

(73) Assignee: LUMENIS LTD. (IL)

( * ) Notice: Subject to any disclaimer, the term of this patent is extended or adjusted under 35 U.S.C. 154(b) by 191 days.

(21) Appl. No.: 13/525,442

(22) Filed: Jun. 18, 2012

(65) Prior Publication Data

US 2013/0338655 A1    Dec. 19, 2013

(51) Int. Cl.
*A61B 18/18* (2006.01)
*A61B 18/22* (2006.01)
*A61B 18/00* (2006.01)

(52) U.S. Cl.
CPC ....... *A61B 18/22* (2013.01); *A61B 2018/00184* (2013.01); *A61B 2018/00577* (2013.01); *A61B 2018/00589* (2013.01); *A61B 2018/00601* (2013.01); *A61B 2018/00821* (2013.01)

(58) Field of Classification Search
CPC ........... A61B 18/00; A61B 2018/0053; A61B 2018/00577; A61B 2018/00; A61B 2018/00601; A61B 2018/00607; A61B 17/28; A61B 17/32; A61B 17/29; A61B 17/2804; A61B 2017/2926
USPC .......... 606/1, 13–19, 139, 144, 167, 170, 190
See application file for complete search history.

(56) References Cited

U.S. PATENT DOCUMENTS

| 4,249,533 | A | * | 2/1981 | Komiya | 606/15 |
| 4,266,547 | A |   | 5/1981 | Komiya |  |
| 5,147,356 | A |   | 9/1992 | Bhatta |  |
| 5,209,747 | A | * | 5/1993 | Knoepfler | 606/16 |
| 5,217,460 | A |   | 6/1993 | Knoepfler |  |
| 5,254,115 | A | * | 10/1993 | Bhatta et al. | 606/16 |

(Continued)

FOREIGN PATENT DOCUMENTS

| DE | 4434938 | 2/1996 |
| JP | 1238852 | 9/1989 |

(Continued)

OTHER PUBLICATIONS

Rosenthal et al., "Laser Thermal Angioplasty Probe (Hot Tip) Temperature: Effects of Flow", "Lasers in Surgery and Medicine 10", Nov. 7, 1989, pp. 124-132, No. 2, Publisher: Wiley-Liss, Inc.

*Primary Examiner* — Ahmed Farah
(74) *Attorney, Agent, or Firm* — ISUS Intellectual Property PLLC

(57) ABSTRACT

Systems and methods for a multifunction surgical apparatus are provided. In one embodiment, a surgical separator comprises: a base; a plurality of separation tongs each movably coupled to the base at their proximal end, wherein the tongs have distal ends each having a blunt profile; a cable coupled to the base, the cable including an optical fiber, where the base is arrange to position the optical fiber to aim an optical energy beam from the optical fiber out from the base and between the tongs at a centered point between the distal ends; wherein the cable further includes at least one element providing a control signal that controls operation of the tongs to move between and open position and a closed position; wherein when the distal ends of each of the tongs are positioned together into the closed position, the exterior profile of the tongs forms a wedge shape having a tip where the tongs meet.

13 Claims, 12 Drawing Sheets

(56) References Cited

U.S. PATENT DOCUMENTS

| | | | |
|---|---|---|---|
| 5,376,094 A | 12/1994 | Kline | |
| 5,607,389 A | 3/1997 | Edwards et al. | |
| 5,797,958 A * | 8/1998 | Yoon | 606/207 |
| 6,039,729 A | 3/2000 | Durville et al. | |
| 6,454,762 B1 | 9/2002 | Rosler et al. | |
| 2001/0041899 A1 | 11/2001 | Foster | |
| 2004/0054377 A1 | 3/2004 | Foster et al. | |
| 2005/0010212 A1 * | 1/2005 | McClurken et al. | 606/51 |
| 2005/0010235 A1 | 1/2005 | VanDusseldorp | |
| 2007/0066985 A1 | 3/2007 | Geitz et al. | |
| 2008/0064982 A1 | 3/2008 | Nowlin et al. | |
| 2008/0077122 A1 | 3/2008 | Boyden et al. | |
| 2012/0053606 A1 * | 3/2012 | Schmitz et al. | 606/167 |

FOREIGN PATENT DOCUMENTS

| | | |
|---|---|---|
| JP | 5161659 | 6/1993 |
| JP | 5337073 | 12/1993 |
| JP | 7132124 | 5/1995 |
| WO | 8909569 | 10/1989 |
| WO | 2010133307 | 11/2010 |

* cited by examiner

SYSTEMS AND METHODS FOR A MULTIFUNCTION SURGICAL APPARATUS

BACKGROUND

Prostate enlargement is a condition that affects many men, including, to some degree, most men over the age of 65 years. There are few methods to treat enlarged prostates. One common procedure is open prostatectomy. Open prostatectomy involves a surgeon, through a lower abdominal incision, manually separating the prostate from the surrounding capsule, and removing it by hand. Another common technique is laser enucleation of the prostate. During this procedure enucleation of the anatomic lobes of the prostate are being enucleated. The enucleation procedure are often accomplished by utilizing laser energy for cutting/ablating portion of the prostate and using the ureteroscope to separate the prostate from the capsule and help pushing it to the bladder. This procedure is less intrusive, involving the delivery of surgical instruments to the prostate region via insertion through the urethra. While the latter procedure does have the advantage of being less intrusive, there is a need to improve the handling of internal bleeding, ablation of the prostate and enucleation and separation of the prostate from the capsule during laser enucleation.

For the reasons stated above and for other reasons stated below which will become apparent to those skilled in the art upon reading and understanding the specification, there is a need in the art for a multifunctional surgical apparatus for use in minimally invasive surgical procedures.

SUMMARY

The Embodiments of the present invention provide for multifunctional surgical apparatus for use in minimally invasive surgical procedures and will be understood by reading and studying the following specification.

A surgical separator, the separator comprising: a base; a plurality of separation tongs each movably coupled to the base at their proximal end, wherein the plurality of separation tongs have distal ends each having a blunt profile; a cable coupled to the base, the cable including an optical fiber, where the base is arrange to position the optical fiber to aim an optical energy beam from the optical fiber out from the base and between the plurality of separation tongs at a centered point between distal ends of the plurality of separation tongs; wherein the cable further includes at least one element providing a control signal that controls operation of the plurality of separation tongs to move between and open position and a closed position; wherein when the distal ends of each of the plurality of separation tongs are positioned together into the closed position, the exterior profile of the plurality of separation tongs forms a wedge shape having a tip where the plurality of separation tongs meet.

DRAWINGS

Embodiments of the present invention can be more easily understood and further advantages and uses thereof more readily apparent, when considered in view of the description of the preferred embodiments and the following figures in which.

In accordance with common practice, the various described features are not drawn to scale but are drawn to emphasize features relevant to the present invention. Reference characters denote like elements throughout figures and text.

DETAILED DESCRIPTION

In the following detailed description, reference is made to the accompanying drawings that form a part hereof, and in which is shown by way of specific illustrative embodiments in which the invention may be practiced. These embodiments are described in sufficient detail to enable those skilled in the art to practice the invention, and it is to be understood that other embodiments may be utilized and that logical, mechanical and electrical changes may be made without departing from the scope of the present invention. The following detailed description is, therefore, not to be taken in a limiting sense.

Figure 1:
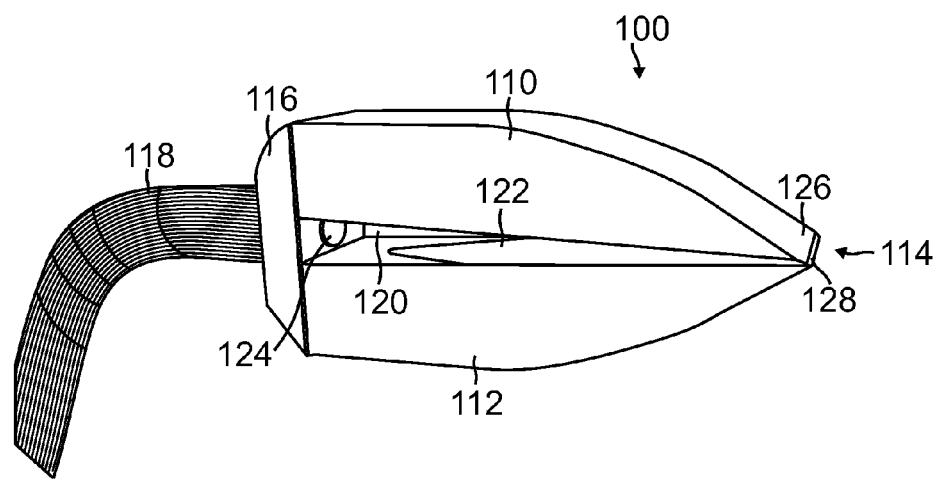
FIGS. 1 and 1A are diagrams of a surgical separator of one embodiment of the present invention.
Figure 1A:
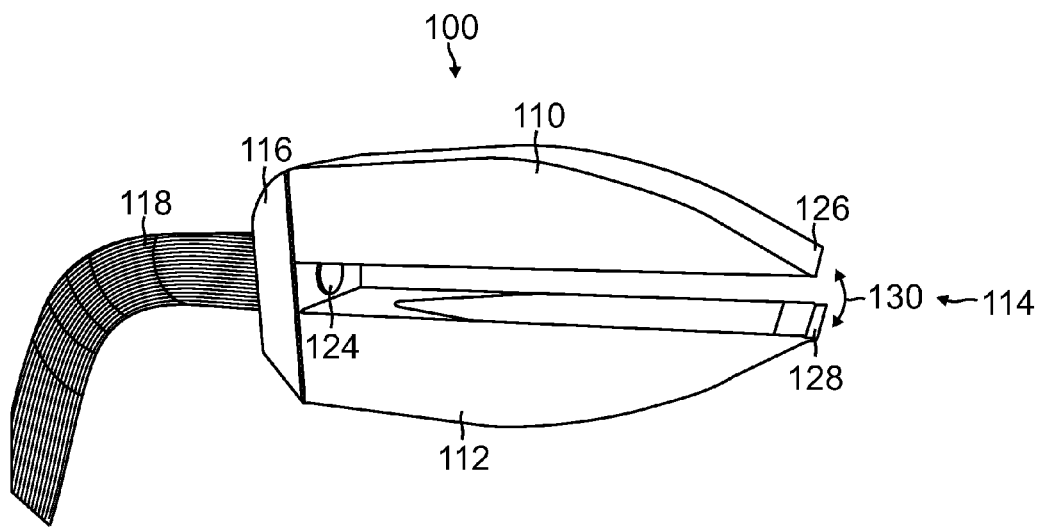

FIGS. 1 and 1A are diagrams illustrating a separator 100 apparatus of one embodiment of the present invention. Separator 100 comprises a plurality of separation tongs including a first separator tong 110 and a second separator tong 112 each pivotally coupled to a base 116. That is, each of the tongs 110, 112 are, at their proximal ends, coupled to opposing ends of base 116 such that they operate as a pair of jaws to open and close. When separator 100 is in the "closed position" the distal ends 126 and 128 of the respective tongs 110 and 112 come together to form a wedge at the tip 114 of separator 100. The "closed position" of separator 100 is illustrated in FIG. 1. When separator 100 is in the "open position", the distal ends 126 and 128 of the respective tongs 110 and 112 are separated from each other by some distance 130. The "open position" of separator 100 is illustrated in FIG. 1A. The distal ends 126 and 128 blunted so that tip 114 does not cut or damage tissue as separator 100 is inserted. Further, in the closed position, the tongs 110 and 112 have a generally wedged shaped profile beginning at tip 114. Further, the tongs 110 and 112 and base 116 of separator 100 are comprised of a material having smooth exterior surface with no sharp edges or corners that would cut or damage tissue during insertion or removal. In one embodiment, inner surfaces 120 and 122 of the separator 100 are coated, such as with a reflective coating, as further discussed below.

Base 116 is further coupled to a cable 118 that includes an optical fiber 124. Base 116 is illustrated in a default position with optical fiber 124 retracted. As further illustrated in FIG. 6, for some embodiments, optical fiber 124 can be pushed out from the base 116 so that an optical energy beam delivered by optical fiber 124 is directed out from base 116 and between ends 128 and 128, aimed at a target tissue in order to, for example, cut, incise, ablate, enucleate or to coagulate the tissue.

Cable 118 further includes wire cables and/or electrical conductors for operating tongs 110 and 112 as described herein. For example, in one embodiment, cable 118 includes wire cables for mechanically manipulating tongs 110 and 112 to place separator 100 into either its open or closed position. In another embodiment, cable 118 includes electrical conductors to provide power and/or control signals to one or more servos used for manipulating the position of tongs 110 and 112.

In another embodiment the lower tong 112 is stabilized while the upper tong 110 is manipulated. In still another embodiment, the upper tong 110 is stabilized while the lower tong 112 is manipulated. In one embodiment, one or both of the tongs 110 and 112 are connected to base 116 and/or each other with springs. In yet another embodiment, cable 118 includes electrical conductors to magnetically control the position of tongs 110 and 112. For example, in one embodiment, tongs 110 and 112 either include magnets, or are themselves magnetized. By controlling the polarity of the magnetic fields, tongs 110 and 112 will either be attracted to each other or repelled from each other to place selector 100 into either the open or closed position.

Further, separator tongs 110 and 112 may optionally be arranged to have a default position that they automatically return to when at rest. For example, in one embodiment, operating tongs 110 and 112 by default remain in the open position unless provided a signal to close. This may be useful where the optical fiber 124 is being utilized for providing a low power aiming beam, or for visualization (each of which are further discussed below). Alternatively, in another embodiment, operating tongs 110 and 112 be default remain in the close position unless provided a signal to open. This embodiment may be useful for embodiments where the tongs should remain closed to permit properly delivery of separator 100 through a passage in the body to a treatment site. One such example is discussed below with respect to FIG. 3, where a separator 100 is inserted in through the urethra.

Figure 2:
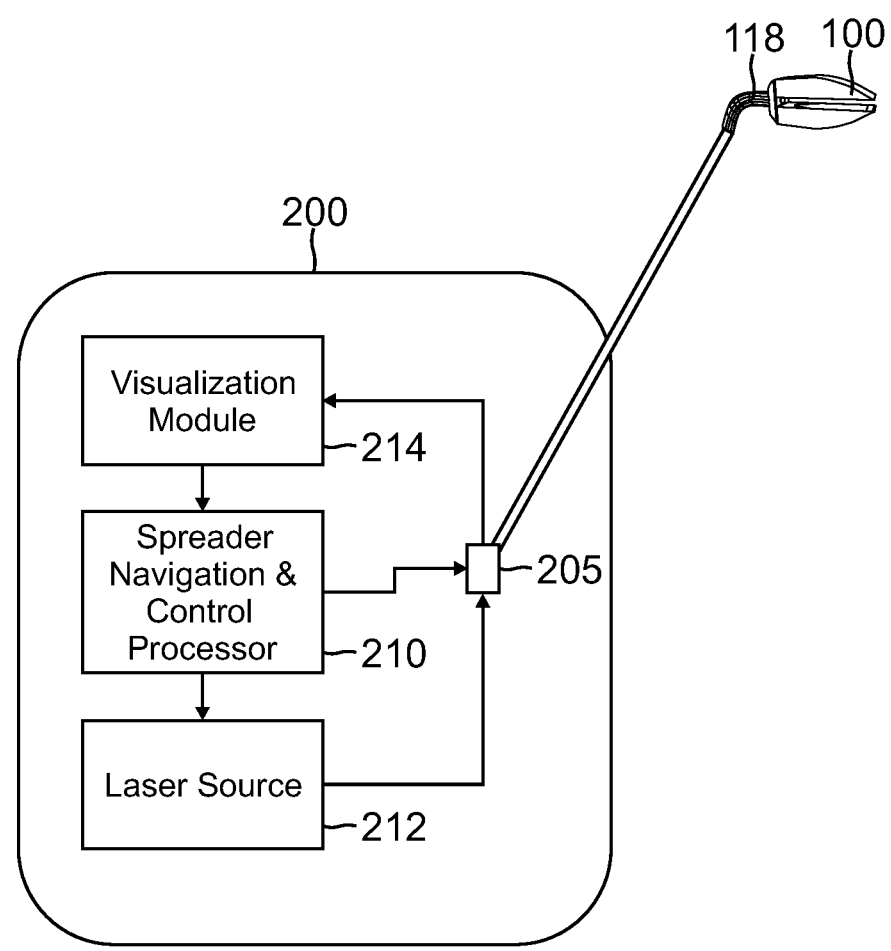
FIG. 2 is a block diagram of system of one embodiment of the present invention for use with the surgical separator of FIG. 1.

FIG. 2 is a block diagram illustrating a system 200 for operating a separator 100 such as discussed in FIGS. 1 and 1A. System 200 comprises a spreader navigation and control processor 210 and a laser source 212, which are each coupled to separator 100 via cable 118. Spreader navigation and control processor 210 provides the functionality necessary to operate tongs 110 and 112 between open and closed positions, and to guide the position of spreader 100 within a patient to the treatment area. Laser source 212 provides optical energy to optical fiber 124 in order to output the laser light from base 116 as discussed above for coagulation or hemostatis. In one embodiment, the optical energy has a volumetric energy density of 160-800 J/cm$^3$ on tissue. For coagulation or hemostatis the laser operates in lower volumetric energy density values of 40-160 J/cm$^3$. Laser source 212 may operate in either continuous wave (CW) mode or pulsed. In one embodiment, in order to operate separator 100 as a coagulator, laser source 212 provides optical energy of sufficient density so that the volumetric energy density values that arrive to the tissue to be treated are in the range of 40-800 J/cm$^3$. In one embodiment, laser source 212 may optionally provide an additional lower power beam of optical energy (i.e., in the milliwatt range) and in a different wavelength at the visible range (for example, red, green or another wavelength) so that separator 100 may emit a lower power beam such as for aiming or illumination at a treatment area. In one embodiment, operation of laser source 212 is controlled by spreader navigation and control processor 210. The laser source 212 may be realized using any form of laser technology such as, but not limited to, solid state, laser diode, fiber laser, gas laser, dye laser, operating in a wavelength range such as 500 nm-11000 nm.

In one embodiment, system 200 further comprises a visualization module 214 coupled to fiber 124 that processes video images received via fiber 124 from spreader 100. In one embodiment, visualization module 214 provides a video display to the operator of spreader 100 so that the operator may more accurately place spreader 100 into the desired position or verify that spreader 100 is in the desired configuration. For example, in one embodiment, visualization module 214 using fiber 124 functions as a camera that permits the operator to verify whether tongs 110 and 112 are either in the opened or closed position. In other embodiment, visualization module 214 provides a feedback signal to spreader navigation & control processor 210 which is used by processor 210 to more accurately control spreader 100. In one embodiment, system 200 further comprises an optical coupler 205 is coupled to fiber 124 to pass optical energy from laser source 212 through fiber 124 to separator 100, as the pass optical imagery received from separator 100 via fiber 124 to visualization module 214. In one embodiment, visualization module 214 and processor 210 are realized by a single integrated component.

Figure 3:
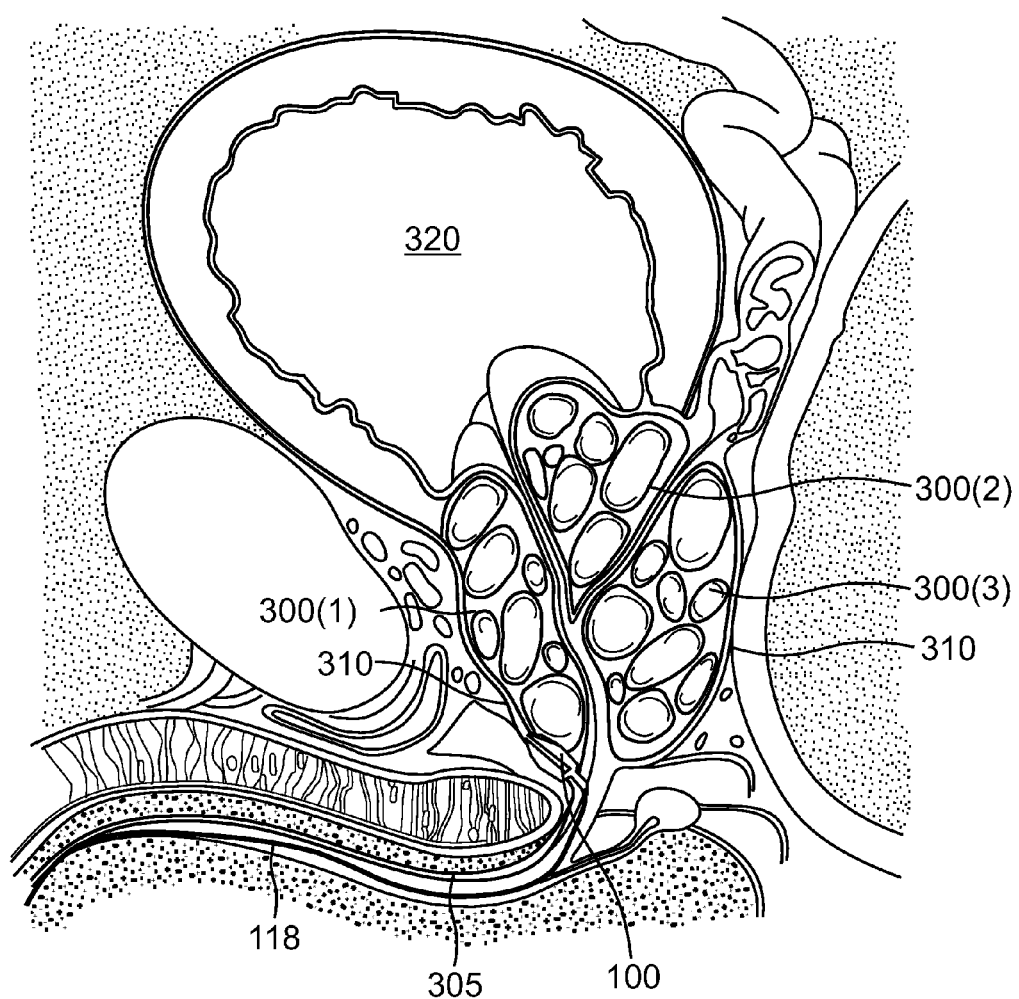
FIG. 3-6A are illustrations of an example prostatectomy procedure performed using a surgical separator of one embodiment of the present invention.
Figure 4:
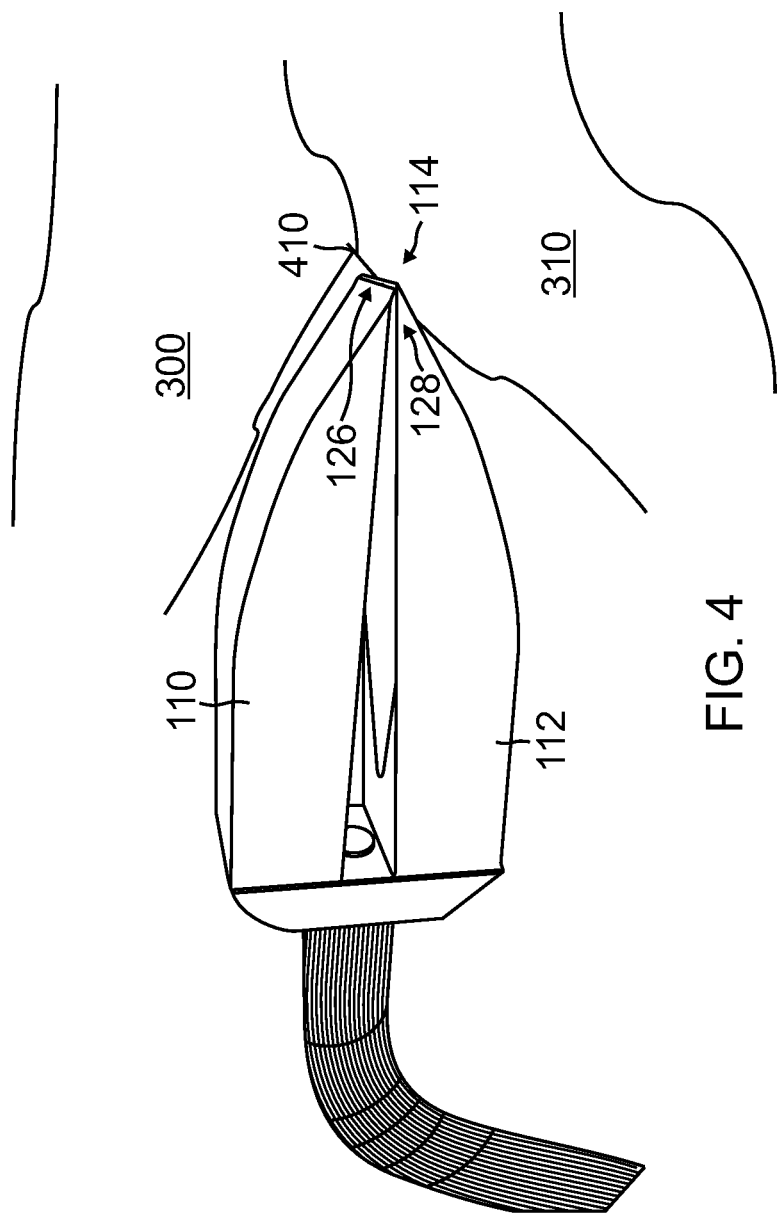
Figure 5:
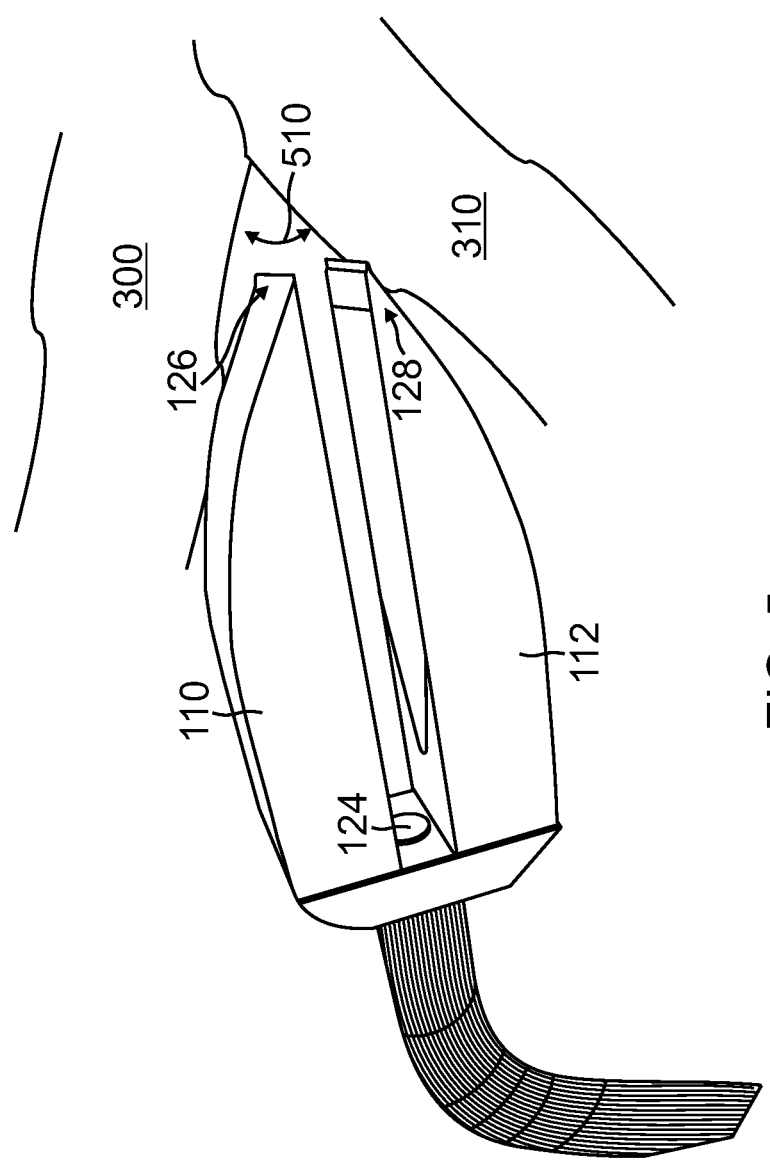

FIGS. 3-6 are diagrams illustrating a minimally invasive prostatectomy using a separator 100 of one embodiment of the present invention. FIG. 3 illustrates the three lobes of a prostate (shown as lobes 300(1), 300(2) and 300(3)) collectively referred to herein as prostate 300. With tongs 110 and 112 in the closed position, separator 100 and cable 118 are inserted through urethra 305. The optical fiber 124 may be first pushed out from base 116 beyond ends 126 and 128 to incise prostate tissues before separation. Then, as illustrated in FIG. 4, separator 100 is positioned to place the closed tip 114 of separator 100 between a portion of the capsule 310 and a lobe of prostate 300. Once in position, the distal ends 126 and 128 of tongs 110 and 112 are slowly opened (as shown in FIG. 5) separating the prostate 300 from the capsule 310 as shown generally at 510. As mentioned above, distal ends 126 and 128 of tongs 110 and 112 are blunted so that the opening of tongs 110 and 112 results in the pulling of the prostate 300 from capsule 310 rather than a cutting of the prostate 300 from capsule 310.

Figure 6:
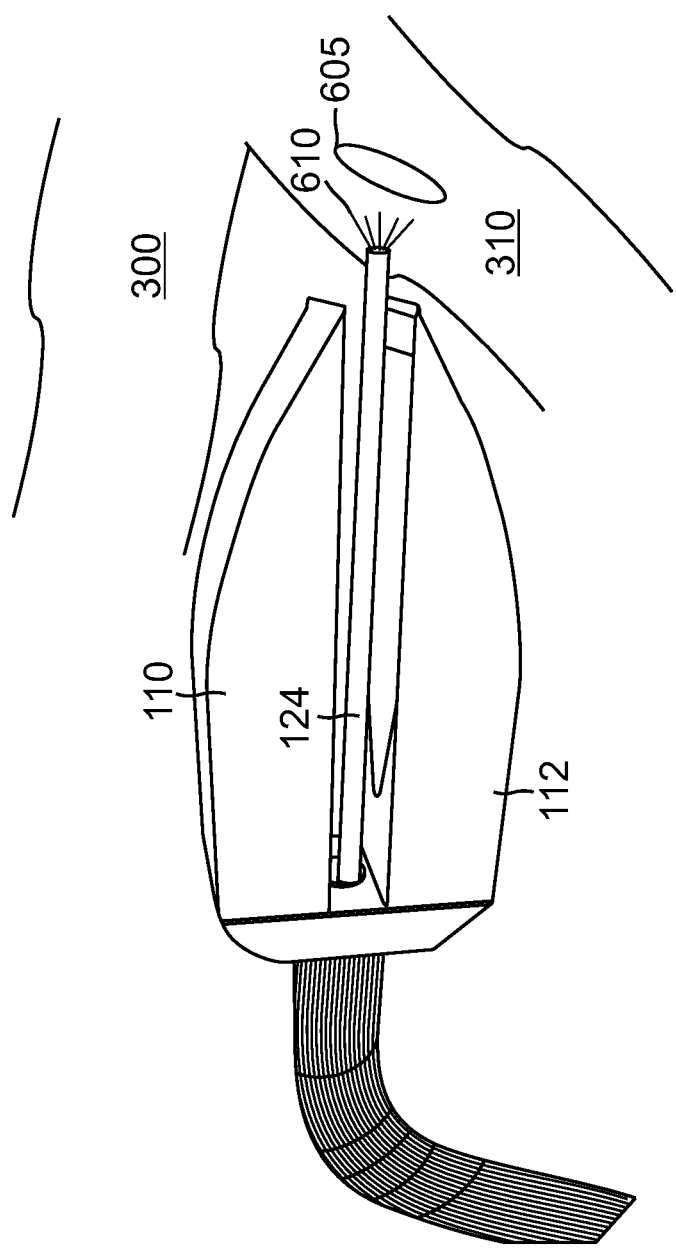
Figure 7:
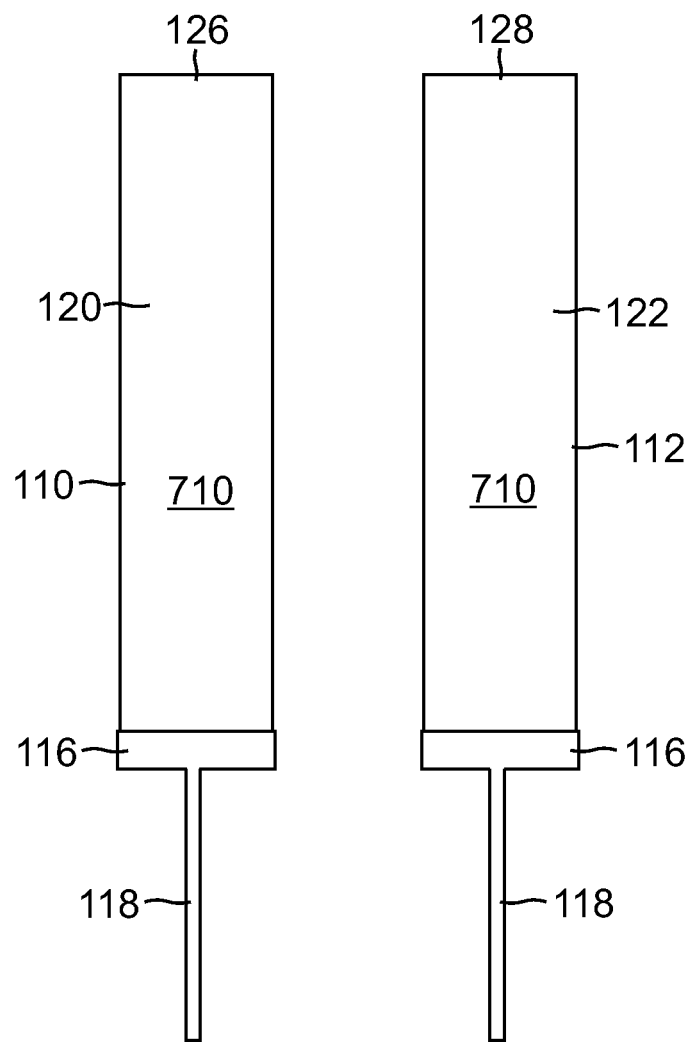
FIG. 7 is a diagram illustrating internal surfaces for tongs of a surgical separator of one embodiment of the present invention.

Nevertheless, bleeding may occur in capsule 310 tissue or in the lobes 300(1), 300(2), 300(3) from which the prostate has been separated. This is illustrated in FIG. 6, where a tear 605 in capsule 310 results in bleeding. In one embodiment, bleeding at tear 605 may be identified by the operator of separator 100 using the visualization module 214 as described above. In one embodiment in order to stop the bleeding, the optical fiber 124 is threaded from base 116 to the bleeding tear 605 so that fiber 124 may deliver energy from the laser source 212 to the optical fiber 124 and operate to coagulate or stop the bleeding using volumetric energy density of 40-800 J/cm$^3$ to the tissue of capsule 310 at tear 605. As would be appreciated by one of ordinary skill in the art after reading this disclosure, laser beam 610 will not be delivered with 100% efficiency because some energy is lost on the fiber and in the medium between the fiber tip and the tear 605 (water, saline, blood, etc.). Depending on the positioning of fiber 124, there can also be absorption of energy by the internal surfaces 120 and 122 of tongs 110 and 120 will also occur. For this reason, in one embodiment as shown in FIG. 7, the internal surface 120 of tong 110 and the internal surface 122 of tong 112 each have a coating 710 with highly reflective properties that inhibit absorption of optical energy from laser beam 610 by the tongs 110 and 112. In one embodiment, coating 710 is a metallic coating.

Figure 6A:
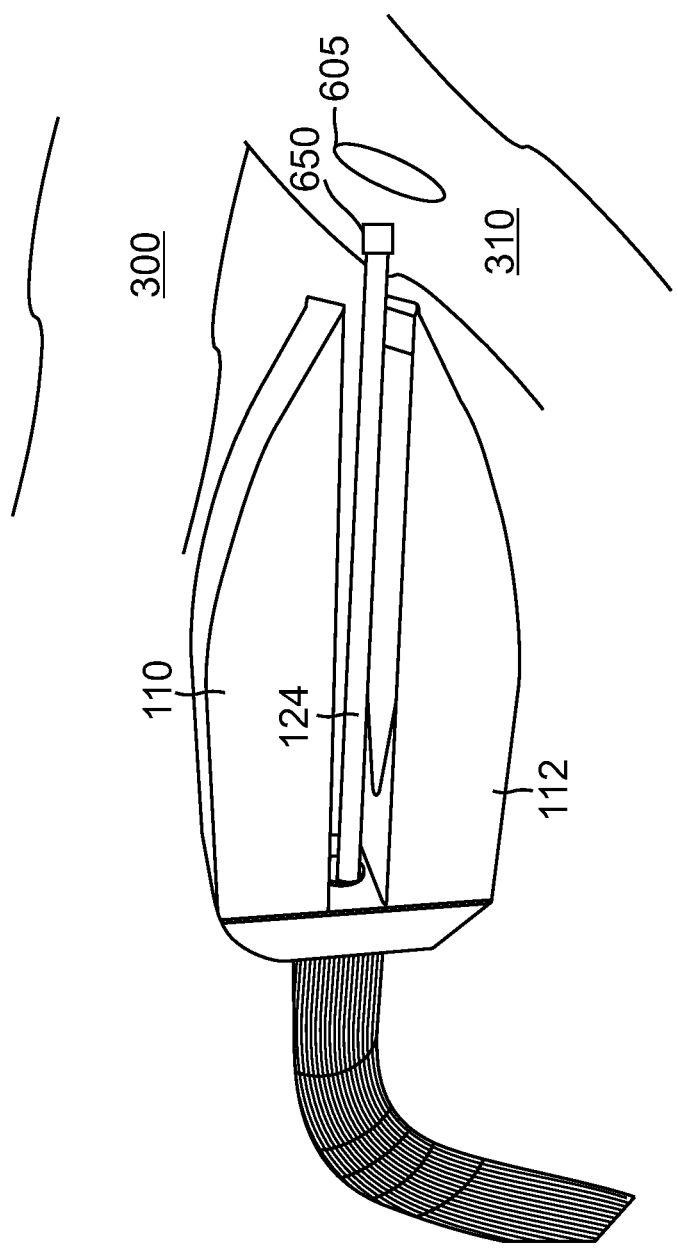

In one alternate embodiment illustrated in FIG. 6A, in order to use the laser energy for hemostasis a cup 650 is attached to the tip of fiber 124. The energy that is delivered through the optical fiber heats this cup 650 to temperature range of 50° C.-200° C. The cup 650 creates hemostasis by contact with the bleeding tissue 605. The cup 650 can be made from metal or other bio-compatible absorptive materials.

Once a lobe, or other portion thereof, of prostate 300 has been completely separated from capsule 310, separator 100 may be used push the separated tissue into bladder 320, where another device may be used to further nucleate and evacuate the tissue using low-level suction.

Figure 8:
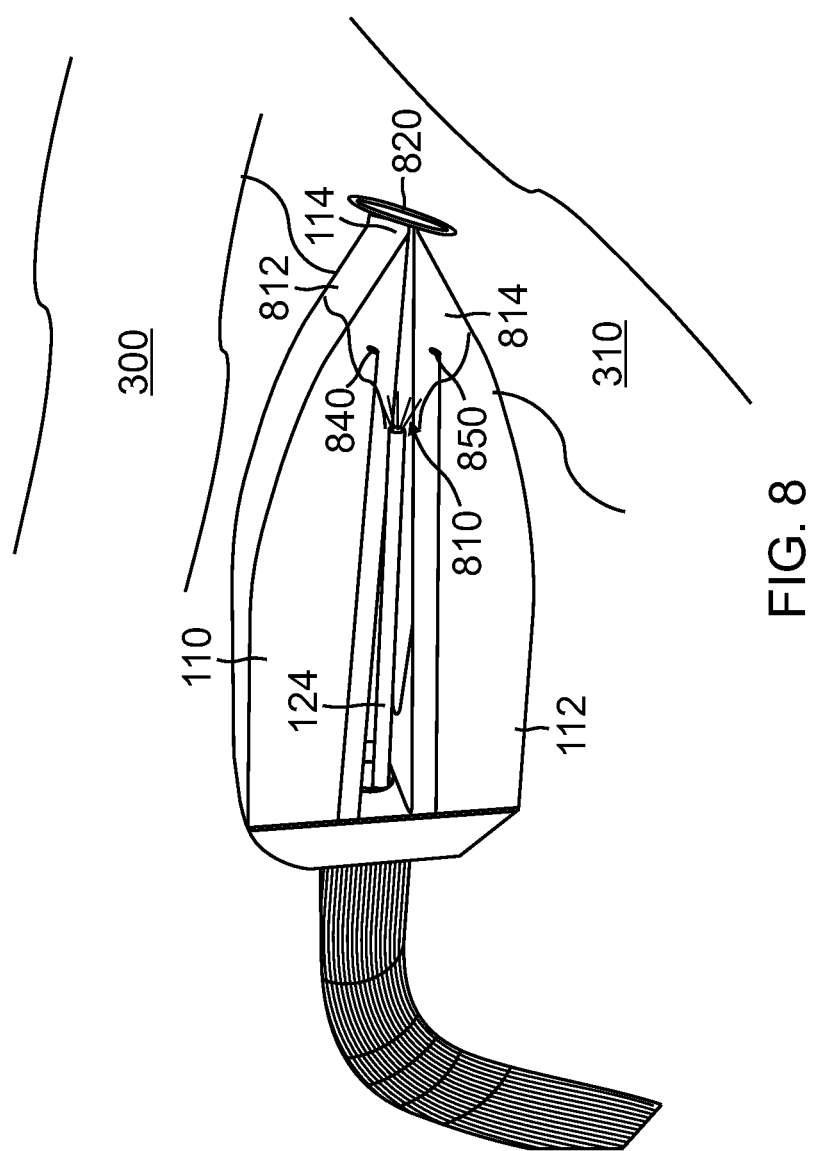
FIG. 8 is an illustration of an alternate procedure using a surgical separator of one embodiment of the present invention.

FIG. 8 illustrates yet another embodiment for using separator 100 to control bleeding when bleeding is occurs. In FIG. 8, a tear 820 in capsule 310 is illustrated where bleeding has occurred. In this embodiment, the optical fiber 124 is threaded to a position within the tongs 110 112 inside the separator 100. The laser source 212 that is coupled to the optical fiber 124 is operated to produce a laser beam 810 with tongs 110 and 112 in the closed position in order to heat regions 812 and 814 on respective distal ends 126 and 128. Regions 812 and 814 absorb energy from laser beam 810 such that the tip 114 of separator 100 reaches a temperature between 50 to 200 degrees Celsius, which is a sufficient temperature to coagulating the bleeding from tear 820 by contacting tip 114 to the tissue at tear 820 This is referred as contacting coagulator. In order to avoid over heating of the regions 812 and 814 two thermocouples 840 and 850 are imbedded inside the regions 812 and 814 and continually monitoring the temperature at the regions 812 and 814. The laser is radiating to stabilize the temperature in a close loop. That is, thermocouples 840 and 850 provide feedback used to control operation of laser source 212 in order to stabilize the temperature at 812 and 814. As would be appreciated by one of ordinary skill in the art after reading this disclosure, the volumetric energy density of laser beam 810 emitted from fiber 124 to produce a temperature between 50 to 200 degrees Celsius at tip 114 will depend on several factors including the absorption coefficient of the medium between the fiber tip and the separators, and the composition, mass, thickness, and geometry of the material making up tongs 110 and 120. However, once these factors are known, the volumetric energy density output needed to produce laser beam 810 can be readily determined. Further, in one implementation of this configuration, tongs 110 and 112 comprise a metal or other material that quickly heat when laser beam 810 is applied and quickly cool once lease beam 810 is discontinued.

Figure 9:
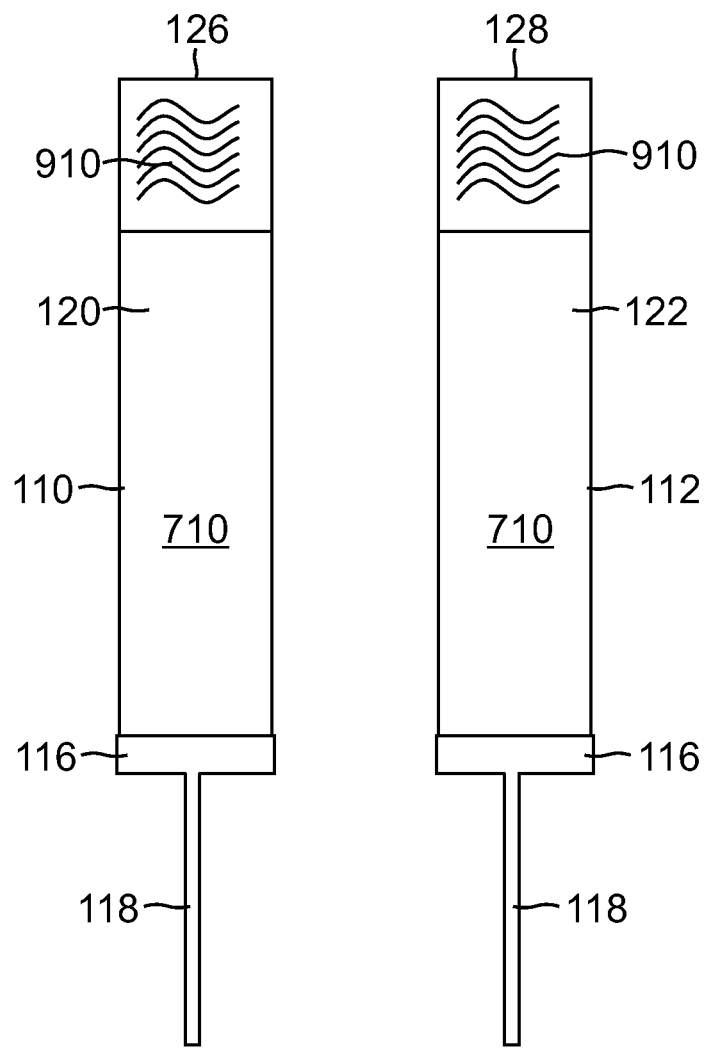
FIG. 9 is a diagram illustrating internal surfaces for tongs of a surgical separator of another embodiment of the present invention.

FIG. 9 illustrates an optional embodiment for separator 100 when used in the manner of the coagulator tip configuration described in FIG. 8. In FIG. 9, the internal surface 120 of tong 110 and the internal surface 122 of tong 112 each have two distinct types of coatings. In order to facilitate absorption of energy from laser beam 810, a region of the internal surfaces 120 and 122 at the distal ends 126 are 128 is provided with a high receptivity coating 910. For example, in one embodiment high receptivity coating 910 creates a rough surface contour that promotes thermal absorption. Further, in order to facilitate delivery of the optical energy to coating 910, the region between coating 910 and base 116 includes a coating 710 with highly reflective properties that inhibit absorption of optical energy from laser beam 810.

Figure 10:
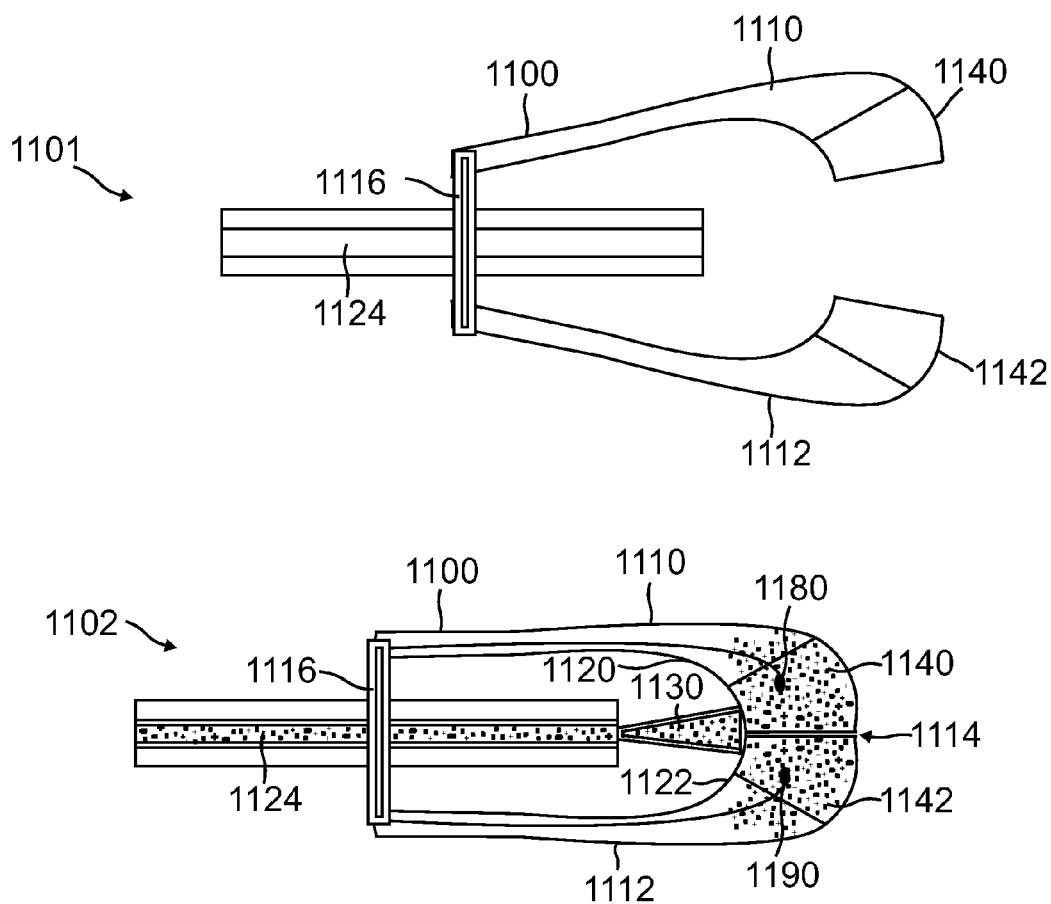
FIG. 10 is a diagram of a surgical apparatus of yet another embodiment of the present invention.

The scope of embodiments of the present invention is not limited to separators such as discussed above as embodiments beyond separators are envisioned. For example FIG. 10 is a diagram illustrating a coagulation apparatus 1100 of one embodiment of the present invention. Coagulation apparatus 1100 comprises a plurality of tongs 1110 and 1112 pivotally coupled to a base 1116 which supports an optical fiber 1124 in the same manner as described above with respect to the like named components of separator 100. FIG. 10 at 1101 illustrates tongs 1110 and 1112 in an open position while tongs 1110 and 1112 are illustrated in a closed position at 1102. In contrast to separator 100, the tongs 1110 and 1112 when closed (as shown at 1102) do not necessarily form a wedge shaped profile. Instead, other profiles may be used depending on the intended application. For example, in various embodiments, tongs 1110 and 1112 may be manipulated between opened and closed (using any of the manners or mechanisms described in any of the embodiments above) to provide functions such as a mechanical spatula or for tissue stretching, cutting or grasping. With tongs 1110 and 1112 in the closed position, coagulation apparatus 1100 may further function in a contacting coagulator configuration. In the same manner as described with respect to FIG. 8, a laser source (such as laser source 212, for example) is operated to produce a laser beam 1130 from fiber 1124 onto the internal surfaces 1120 and 1122 of tongs 1110 and 1112. Regions 1140 and 1142 absorb energy from laser beam 1130 such that the tip 1114 of apparatus 1100 reaches a temperature between 60 to 80 degrees Celsius, which is a sufficient temperature to coagulate bleeding when placed in contact with a bleeding tissue. In order to avoid over heating of the regions 1140 and 1142 two thermocouples 1180 and 1190 are embedded inside the regions 1110 and 1112 and continually monitoring the temperature at the regions 1140 and 1142. The laser is radiating to stabilize the temperature in a close loop. That is, thermocouples 1180 and 1190 provide feedback used to control operation of laser source 212 in order to stabilize the temperature at 812 and 814. As would be appreciated by one of ordinary skill in the art after reading this disclosure, the volumetric energy density of laser beam 1130 emitted from fiber 1124 to produce a temperature between 50 to 200 degrees Celsius at tip 1114 will depend on several factors including the distance laser beam 1130 must travel and absorption coefficient of the medium in this optical path between the fiber tip and the separators, mass, thickness, and geometry of the material making up tongs 1110 and 1120. However, once these factors are known, the volumetric energy density output needed to produce laser beam 1130 can be readily determined. Further, in one implementation of this configuration, tongs 1110 and 1112 comprise a metal or other material that quickly heat when laser beam 1130 is applied, and quickly cool once lease beam 1130 is discontinued. Further, surfaces 1120 and 1122 may be treated with a high receptivity coating, such as describe with respect to coating 910 described above, for example.

Figure 11:
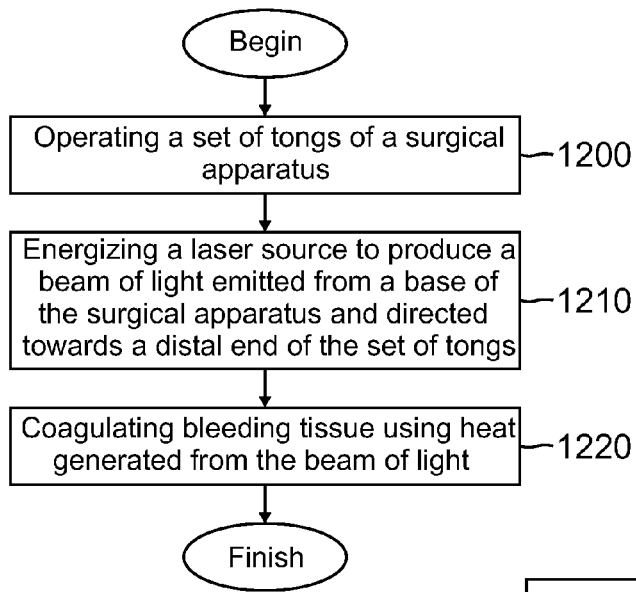
FIG. 11 is a flow chart illustrating a method of one embodiment of the present invention.

FIG. 11 is a flow chart illustrating a method for coagulating blood from a bleeding tissue. In alternate embodiments, the method may be performed using an apparatus such as, but not limited to, the separator 100 or coagulation apparatus 1100.

The method begins at 1200 with operating a set of tongs of a surgical apparatus. In one embodiment, the surgical apparatus comprises as set of tongs including a first tong and a second tong each pivotally coupled to a base. That is, each of the tongs are, at their proximal ends, coupled to opposing ends of the base such that they operate as a pair of jaws to open and close. When the surgical apparatus is in the "closed position" the distal ends of the respective tongs come together. When the surgical apparatus is in the "open position", the distal ends of the respective tongs are separated from each other by some distance.

The method proceeds to 1210 with energizing a laser source to produce a beam of light emitted from a base of the surgical apparatus and directed towards a distal end of the set of tongs. For example, in one embodiment where the tongs are placed in the open position at block 1200, the beam of light is directed to pass between the distal ends such as illustrated and described with respect to FIG. 6. In another embodiment where the tongs are place in the closed position at block 1200, energy from the beam of light is absorbed by the distal ends of the tongs resulting in their heating, such as illustrated and describe with respect to FIG. 10. In alternate embodiments, the beam of light may comprises either a continuous wavelength (CW) laser beam or a pulsed mode laser beam.

The method next proceeds to 1220 with coagulating bleeding tissue using heat generated from the beam of light. For example, in the embodiment where the tongs are placed in the open position and the beam of light is directed to pass between the distal ends, energy from the light is directly used to treat and coagulate bleeding from a tissue. In one such embodiment, block 1220 further comprises providing a beam of light that delivers in the range of 40-800 J/cm$^3$ to the tissue. In the embodiment where the tongs are place in the closed position and the beam of light is absorbed by the distal ends of the tongs, the tongs are heated by the beam and coagulating bleeding tissue further comprises contacting the distal ends of the tongs to the bleeding tissue. In one such embodiment, block 1220 further comprises heating the distal ends of the tongs in the range of 50-200 degrees Celsius.

Figure 12:
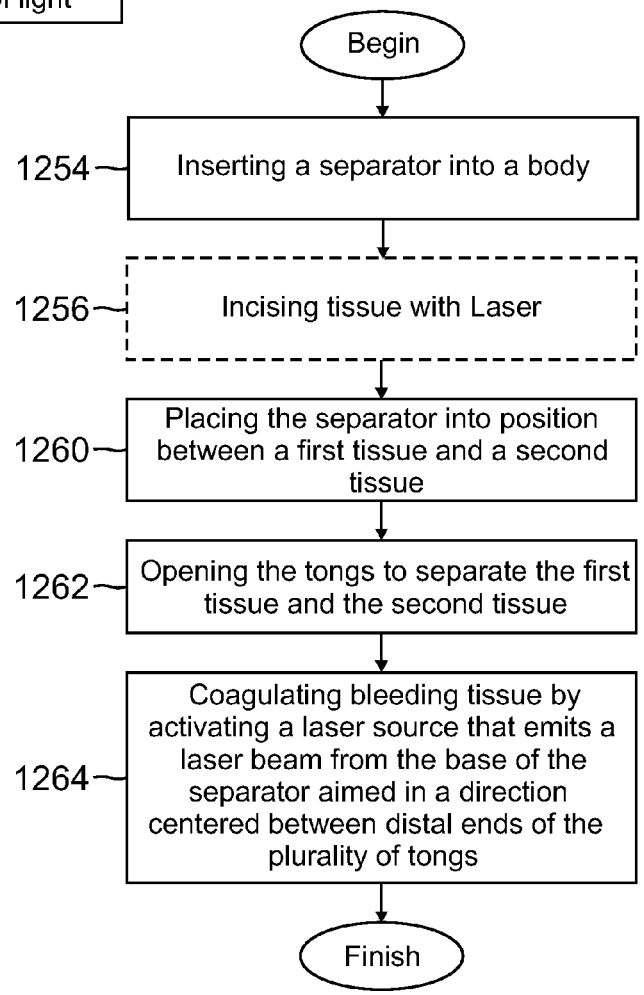
FIG. 12 is a flow chart illustrating a method of one embodiment of the present invention.

FIG. 12 is a flow chart illustrating a method for performing a surgical procedure of one embodiment of the present invention. In alternate embodiments, the method may be performed using an apparatus such as any of the embodiments of separator 100 described above. The method begins at 1254 with inserting a separator into a body. For example, for prostate surgery, inserting the separator includes inserting the separator through the urethra to the closest place of the prostate. In that case, the method may optionally proceed to 1256 with incising tissue (for the prostate boundaries) with the laser. This can be done by threading the optical fiber 124 out from base 116. After incising tissue is complete, the optical fiber is pulled back into base 116.

The separation begins at 1260 with placing the separator into position between a first tissue and a second tissue. In one embodiment, the separator comprises a plurality of separation tongs including a first separator tong and a second separator tong each pivotally coupled to a base. That is, each of the tongs are, at their proximal ends, coupled to opposing ends of the base such that they operate as a pair of jaws to open and close. When the separator is in the "closed position" the distal ends of the respective tongs come together to form a wedge at the tip of the separator. When the separator is in the "open position", the distal ends of the respective tongs are separated from each other by some distance. In one embodiment, the method of FIG. 12 is performed using separator 100 discussed above. In one embodiment, the distal ends are blunted so that the tip of the separator does not cut or damage tissue as the separator is inserted and placed into position. Further, in the closed position, the tongs have a generally wedged shaped profile and with the base are comprised of a material having smooth exterior surface with no sharp edges or corners that would cut or damage tissue during insertion or removal of the separator. The method proceeds to 1262 with opening the tongs to separate the first tissue and the second tissue. This step is illustrated and described with greater detail above with respect to FIG. 5. The method proceeds to 1264 with coagulating bleeding tissue by activating a laser source that emits a laser beam from the base of the separator in the direction of the distal ends. In one embodiment, block 1264 further comprises applying energy from the laser beam directly to the bleeding tissue as described with respect to FIG. 6. In another embodiment, block 1264 further comprises heating the distal ends of the separator and treating the bleeding tissue by contacting the tissue with the heated tongs of the separator as detailed with respect to FIG. 8.

Example Embodiments

Example 1 includes a surgical separator, the separator comprising: a base; a plurality of separation tongs each movably coupled to the base at their proximal end, wherein the plurality of separation tongs have distal ends each having a blunt profile; and a cable coupled to the base, the cable including an optical fiber, where the base is arrange to position the optical fiber to aim an optical energy beam from the optical fiber out from the base and between the plurality of separation tongs at a centered point between distal ends of the plurality of separation tongs; wherein the cable further includes at least one element providing a control signal that controls operation of the plurality of separation tongs to move between and open position and a closed position; and wherein when the distal ends of each of the plurality of separation tongs are positioned together into the closed position, the exterior profile of the plurality of separation tongs forms a wedge shape having a tip where the plurality of separation tongs meet.

Example 2 comprises the separator of example 1, wherein the cable comprises wires that provide a mechanical control signal that controls operation of the separation tongs.

Example 3 comprises the separator of any of examples 1-2, further comprising at least one servo arranged to operate the plurality of separation tongs to move between and open position and a closed position, wherein the at least one servo is controlled by the at least one element.

Example 4 comprises the separator of any of examples 1-3, further comprising at least one magnet arranged to operate the plurality of separation tongs to move between and open position and a closed position, wherein the at least one magnet is controlled by the at least one element.

Example 5 comprises the separator of any of examples 1-4, wherein the plurality of separation tongs and the base are comprised of a material having smooth exterior surface.

Example 6 comprises the separator of any of examples 1-5, wherein the plurality of separation tongs are arranged to default to the closed position.

Example 7 comprises the separator of any of examples 1-6, wherein the plurality of separation tongs are arranged to default to the open position.

Example 8 comprises the separator of any of examples 1-7, wherein each of the plurality of separation tongs further comprises an internal surface that faces the optical energy beam, wherein the surface includes a coating having reflective properties that inhibit absorption of optical energy from the optical energy beam.

Example 9 comprises the separator of any of examples 1-8, wherein each of the plurality of separation tongs further comprises a thermally receptive coating at their distal ends.

Example 10 comprises the separator of any of examples 1-9, wherein the optical fiber is coupled to a laser source that provides the optical energy beam, wherein laser source is calibrated such that the optical energy beam delivers a volumetric energy density in the range of 40-800 J/cm³ to a target tissue when the plurality of separation tongs are in the open position.

Example 11 comprises the separator of any of examples 1-10, wherein the optical fiber is coupled to a laser source that provides the optical energy beam, wherein laser source is calibrated such that the optical energy beam delivers an volumetric energy density that heats the tip to a temperature in the range of 50 to 200 degrees Celsius.

Example 12 comprises the separator of any of examples 1-11, the plurality of separation tongs further comprising: at least one thermocouple embedded within a first tong of the plurality of tongs and arrange to monitor a temperature of the first tong.

Example 13 comprises the separator of any of examples 1-12, wherein the optical fiber is extendable out from the base.

Example 14 comprises the separator of any of examples 1-13, wherein the optical fiber is extendable out from the base between the plurality of separation tongs to a centered point between distal ends of the plurality of separation tongs.

Example 15 includes a surgical apparatus, the apparatus comprising: a base; a plurality of tongs each movably coupled to the base at their proximal end, wherein the plurality of tongs have distal ends each having a blunt profile; and a cable coupled to the base, the cable including an optical fiber, where the base is arrange to position the optical fiber to aim an optical energy beam from the optical fiber out from the base and between the plurality of tongs at a centered point at the distal ends of the plurality of tongs, wherein the cable further includes at least one element providing a control signal that controls operation of the plurality of tongs to move between and open position and a closed position; wherein the optical fiber is coupled to a laser source that provides the optical energy beam, wherein the laser source is calibrated such that the optical energy beam heats an external surface of distal ends of the plurality of tongs.

Example 16 comprises the separator of example 15, wherein the laser source is calibrated such that the optical energy beam heats the external surface of distal ends of the plurality of tongs to a temperature in the range of 50 to 200 degrees Celsius.

Example 17 comprises the separator of any of examples 15-16, wherein the cable comprises wires that provide a mechanical control signal that controls operation of the tongs.

Example 18 comprises the separator of any of examples 15-17, further comprising at least one servo arranged to operate the plurality of tongs to move between and open position and a closed position, wherein the at least one servo is controlled by the at least one element.

Example 19 comprises the separator of any of examples 15-18, further comprising at least one magnet arranged to operate the plurality of tongs to move between and open position and a closed position, wherein the at least one magnet is controlled by the at least one element.

Example 20 comprises the separator of any of examples 15-19, wherein the plurality of tongs and the base are comprised of a material having smooth exterior surface.

Example 21 comprises the separator of any of examples 15-20, wherein the plurality of tongs are arranged to default to the closed position.

Example 22 comprises the separator of any of examples 15-21, wherein the plurality of tongs are arranged to default to the open position.

Example 23 comprises the separator of any of examples 15-22, wherein each of the plurality of tongs further comprises an internal surface that faces the optical energy beam, wherein the surface includes a coating having reflective properties that inhibit absorption of optical energy from the optical energy beam.

Example 24 comprises the separator of any of examples 15-23, wherein each of the plurality of separator tongs comprises a thermally receptive coating at their distal ends.

Example 25 comprises the separator of any of examples 15-24, the plurality of tongs further comprising: at least one thermocouple embedded within a first tong of the plurality of tongs and arrange to monitor a temperature of the first tong.

Example 26 comprises the separator of any of examples 15-25, wherein the optical fiber is extendable out from the base.

Example 27 includes a system comprising: a laser source; a processor coupled to the laser source; and a surgical separator coupled to the processor and the laser source via a cable; the surgical separator comprising: a base; and a plurality of separation tongs each movably coupled to the base at their proximal end, wherein the plurality of separation tongs have distal ends each having a blunt profile; wherein the cable is coupled to the base, the cable including an optical fiber coupled to the laser source, where the base is arrange to position the optical fiber to aim an optical energy beam from the optical fiber out from the base and between the plurality of tongs at a centered point between the distal ends of the plurality of separation tongs; wherein the cable further includes at least one element providing a control signal from the processor that controls operation of the plurality of tongs to move between an open position and a closed position; wherein when the distal ends of each of the plurality of separation tongs are positioned together into the closed position, the exterior profile of the plurality of separation tongs forms a wedge shape having a tip where the plurality of separation tongs meet.

Example 28 includes the system of example 27, wherein the laser source includes at least one calibration setting such that the optical energy beam delivers a volumetric energy density that heats the tip to a temperature in the range of 50 to 200 degrees Celsius when the plurality of separation tongs are in the closed position.

Example 29 includes the system of any of examples 27-28, wherein the laser source includes at least one calibration setting such that the optical energy beam delivers a volumetric energy density in the range of 40-800 J/cm³ to a target tissue when the plurality of separation tongs are in the open position.

Example 30 includes the system of any of examples 27-29, wherein the laser source includes at least one calibration setting such that the optical energy beam delivers a low power aiming beam.

Example 31 includes the system of any of examples 27-30, wherein the cable communicates either an electrical control signal or a mechanical control signal that controls operation of the tongs.

Example 32 includes the system of any of examples 27-31, wherein the plurality of tongs are arranged to default to the closed position when no control signal is provided by the processor.

Example 33 includes the system of any of examples 27-32, wherein the plurality of tongs are arranged to default to the open position when no control signal is provided by the processor.

Example 34 includes the system of any of examples 27-33, wherein each of the plurality of tongs further comprises an internal surface that faces the optical energy beam, wherein the surface includes a coating having reflective properties that inhibit absorption of optical energy from the optical energy beam.

Example 35 includes the system of any of examples 27-34, wherein each of the plurality of separator tongs further comprises a thermally receptive coating at their distal ends.

Example 36 includes the system of any of examples 27-35, further comprising a visualization module coupled to the optical fiber, wherein the visualization modules processes visual images received from the separator.

Example 37 includes the system of any of examples 27-36, wherein the visualization module displays the visual images received from the separator.

Example 38 includes the system of any of examples 27-37, the plurality of separation tongs further comprising: at least one thermocouple embedded within a first tong of the plurality of tongs and arrange to monitor a temperature of the first tong; wherein the laser source controls operation of the optical energy beam based on a temperature signal from the at least one thermocouple.

Example 39 includes the system of any of examples 27-38, wherein the optical fiber is extendable out from the base.

Example 40 includes a method for performing tissue separation, the method comprising: inserting a separator into a body; placing a separator into position between a first tissue and a second tissue, wherein the separator comprises a plurality of separation tongs each movably coupled to a base; opening the tongs to separate the first tissue and the second tissue; and coagulating bleeding tissue by activating a laser source that emits a laser beam from the base of the separator aimed in a direction centered between distal ends of the plurality of tongs.

Example 41 includes the method of example 40, wherein placing the separator into position between the first tissue and the second tissue further comprises placing the separator with the plurality of tongs in a closed position between the first tissue and the second tissue; wherein when the distal ends of each of the plurality of separation tongs are positioned together into the closed position, an exterior profile of the plurality of separation tongs forms a wedge shape having a tip where the plurality of separation tongs meet.

Example 42 includes the method of any of examples 40-41, wherein coagulating bleeding tissue by activating the laser source further comprises applying energy from the laser beam directly to bleeding tissue.

Example 43 includes the method of any of examples 40-42, wherein applying energy from the laser beam directly to bleeding tissue further comprises delivering a volumetric energy density in a range of 40-800 J/cm$^3$ to a target tissue with the plurality of separation tongs in an open position.

Example 44 includes the method of any of examples 40-43, wherein coagulating bleeding tissue by activating the laser source further comprises heating a tip of the separator at the distal ends with the laser beam and treating the bleeding tissue by contacting the bleeding tissue with the tip.

Example 45 includes the method of any of examples 40-44, further comprising heating the tip of the separator to a temperature in the range of 50 to 250 degrees Celsius with the plurality of separation tongs are in an closed position.

Example 46 includes the method of any of examples 40-45, further comprising: threading an optical fiber out from the base, wherein the laser beam is delivered by the optical fiber; incising at least the first tissue with the laser beam; and retracting the optical fiber back into the base.

Example 47 includes the method of any of examples 40-46, further comprising: monitoring a temperature of the plurality of separation tongs; and controlling operation of the laser source based on the temperature.

Example 48 includes a blood coagulation method, the method comprising: operating a set of tongs of a surgical apparatus, wherein the set of tongs are each movably coupled to a base; energizing a laser source to produce a beam of light emitted from the base of the surgical apparatus and directed towards a distal end of the set of tongs; and coagulating bleeding tissue using heat generated from the beam of light.

Example 49 includes the method of example 48, wherein the beam of light is either a continuous wavelength laser beam or a pulsed mode laser beam.

Example 50 includes the method of any of examples 48-49, where the set of tongs are operated to place the set of tongs onto an open position; and wherein the beam of light is directed to pass between the distal ends to directly treat the bleeding tissue.

Example 51 includes the method of any of examples 48-50, wherein the beam of light delivers a volumetric energy density in a range of 40-800 J/cm$^3$ to a target tissue.

Example 52 includes the method of any of examples 48-51, where the set of tongs are operated to place the set of tongs onto a closed position; and wherein energy from the beam of light is absorbed by the distal ends of the set of tongs resulting in a heating of a tip of the surgical apparatus.

Example 53 includes the method of any of examples 48-52, where the tip of the surgical apparatus is heated to a temperature in the range of 50 to 200 degrees Celsius.

Example 54 includes the method of any of examples 48-53, further comprising: threading an optical fiber out from the base, wherein the laser beam is delivered by the optical fiber; incising at least the first tissue with the laser beam; and retracting the optical fiber back into the base.

Example 55 includes the method of any of examples 48-54, further comprising: monitoring a temperature of the plurality of separation tongs; and controlling operation of the laser source based on the temperature.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

What is claimed is:

1. A surgical separator, the separator comprising:
   a base;
   a plurality of separation tongs each movably coupled to the base at their proximal end, wherein the plurality of separation tongs have distal ends each having a blunt profile; and
   a cable coupled to the base, the cable including an optical fiber, where the base is arranged to position the optical fiber to aim an optical energy beam from the optical fiber out from the base and between the plurality of separation tongs at a centered point between distal ends of the plurality of separation tongs;
   wherein the cable further includes at least one element providing a control signal that controls operation of the plurality of separation tongs to move between and open position and a closed position;
   wherein when the distal ends of each of the plurality of separation tongs are positioned together into the closed position, the exterior profile of the plurality of separation tongs forms a wedge shape having a tip where the plurality of separation tongs meet; and at least one thermocouple embedded within a first tong of the plurality of tongs and arranged to monitor a temperature of the first tong.

2. The separator of claim 1, wherein the cable comprises wires that provide a mechanical control signal that controls operation of the separation tongs.

3. The separator of claim 1, further comprising at least one servo arranged to operate the plurality of separation tongs to move between and open position and a closed position, wherein the at least one servo is controlled by the at least one element.

4. The separator of claim 1, wherein the plurality of separation tongs and the base are comprised of a material having smooth exterior surface.

5. The separator of claim 1, wherein the plurality of separation tongs are arranged to default to the closed position.

6. The separator of claim 1, wherein the plurality of separation tongs are arranged to default to the open position.

7. The separator of claim 1, wherein the optical fiber is coupled to a laser source that provides the optical energy beam, wherein laser source is calibrated such that the optical energy beam delivers a volumetric energy density in the range of 40-800 J/cm3 to a target tissue when the plurality of separation tongs are in the open position.

8. The separator of claim 1, wherein the optical fiber is coupled to a laser source that provides the optical energy beam, wherein laser source is calibrated such that the optical energy beam delivers an volumetric energy density that heats the tip to a temperature in the range of 50 to 200 degrees Celsius.

9. The separator of claim 1, wherein the optical fiber is extendable out from the base.

10. The separator of claim 9, wherein the optical fiber is extendable out from the base between the plurality of separation tongs to a centered point between distal ends of the plurality of separation tongs.

11. A surgical separator, the separator comprising:
a base;
a plurality of separation tongs each movably coupled to the base at their proximal end, wherein the plurality of separation tongs have distal ends each having a blunt profile; and
a cable coupled to the base, the cable including an optical fiber, where the base is arranged to position the optical fiber to aim an optical energy beam from the optical fiber out from the base and between the plurality of separation tongs at a centered point between distal ends of the plurality of separation tongs;
wherein the cable further includes at least one element providing a control signal that controls operation of the plurality of separation tongs to move between and open position and a closed position
wherein when the distal ends of each of the plurality of separation tongs are positioned together into the closed position, the exterior profile of the plurality of separation tongs forms a wedge shape having a tip where the plurality of separation tongs meet;
at least one thermocouple embedded within a first tong of the plurality of tongs and arranged to monitor a temperature of the first tong; and
the plurality of separation tongs further comprising at least one magnet arranged to operate the plurality of separation tongs to move between and open position and a closed position, wherein the at least one magnet is controlled by the at least one element.

12. A surgical separator, the separator comprising:
a base;
a plurality of separation tongs each movably coupled to the base at their proximal end, wherein the plurality of separation tongs have distal ends each having a blunt profile; and
a cable coupled to the base, the cable including an optical fiber, where the base is arranged to position the optical fiber to aim an optical energy beam from the optical fiber out from the base and between the plurality of separation tongs at a centered point between distal ends of the plurality of separation tongs;
wherein the cable further includes at least one element providing a control signal that controls operation of the plurality of separation tongs to move between and open position and a closed position;
wherein when the distal ends of each of the plurality of separation tongs are positioned together into the closed position, the exterior profile of the plurality of separation tongs forms a wedge shape having a tip where the plurality of separation tongs meet;
at least one thermocouple embedded within a first tong of the plurality of tongs and arranged to monitor a temperature of the first tong; and
the plurality of separation tongs wherein each of the plurality of separation tongs further comprises an internal surface that faces the optical energy beam, wherein the surface includes a coating having reflective properties that inhibit absorption of optical energy from the optical energy beam.

13. The separator of claim 12, wherein each of the plurality of separation tongs further comprises a thermally receptive coating at their distal ends.

* * * * *